United States Patent
Nagaoka et al.

(10) Patent No.: US 9,630,181 B2
(45) Date of Patent: Apr. 25, 2017

(54) PLUG APPLICATION AND REMOVAL DEVICE AND SAMPLE PROCESSING DEVICE

(75) Inventors: Yoshihiro Nagaoka, Tokyo (JP); Kenichi Takahashi, Tokyo (JP); Toshiki Yamagata, Tokyo (JP); Shigeki Yamaguchi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/240,087

(22) PCT Filed: Aug. 22, 2012

(86) PCT No.: PCT/JP2012/071134
§ 371 (c)(1),
(2), (4) Date: Feb. 21, 2014

(87) PCT Pub. No.: WO2013/027747
PCT Pub. Date: Feb. 28, 2013

(65) Prior Publication Data
US 2014/0212344 A1 Jul. 31, 2014

(30) Foreign Application Priority Data

Aug. 22, 2011 (JP) .................................. 2011-180099

(51) Int. Cl.
*B01L 3/00* (2006.01)
*G01N 35/04* (2006.01)
(Continued)

(52) U.S. Cl.
CPC ................ *B01L 3/56* (2013.01); *G01N 35/04* (2013.01); *B01L 3/0289* (2013.01);
(Continued)

(58) Field of Classification Search
CPC ........... G01N 35/1002; G01N 35/1016; G01N 35/1009; G01N 1/38; G01N 35/00584; B01L 3/0289
(Continued)

(56) References Cited

U.S. PATENT DOCUMENTS 3,842,680 A * 10/1974 Vollick et al. ............. 73/864.22
3,917,455 A * 11/1975 Bak et al. ...................... 422/64
(Continued)

FOREIGN PATENT DOCUMENTS

JP 57-41162 U 3/1982
JP 02/31165 A 2/1990
(Continued)

OTHER PUBLICATIONS

Extended European Search Report received in corresponding European Application No. 12825271.5 dated May 15, 2015.

*Primary Examiner* — Dennis M White
*Assistant Examiner* — Bryan Kilpatrick
(74) *Attorney, Agent, or Firm* — Mattingly & Malur, PC

(57) ABSTRACT

The present invention is such a plug application and removal device that mist which is generated upon plug removal of a sample container or a reagent container is not peripherally scattered, or is such a sample processing device that mist which is generated upon dispensing of a sample or a reagent into a container is not mixed to another container. A plug application and removal device has a container holding mechanism that holds a container housing liquid inside and applied with a plug, and has a plug application and removal mechanism that removes or applies the plug from/to the container. The plug application and removal device has: a control mechanism for controlling movement of liquid or mist spilled out of the container upon a process of removal or application of the plug by the plug application and removal mechanism.

12 Claims, 15 Drawing Sheets

(51) Int. Cl.
   *B67C 3/24* (2006.01)
   *B01L 3/02* (2006.01)
   *G01N 35/10* (2006.01)

(52) U.S. Cl.
   CPC .......... *B01L 2300/042* (2013.01); *B67C 3/24* (2013.01); *G01N 35/1002* (2013.01); *G01N 35/1009* (2013.01); *G01N 35/1016* (2013.01); *G01N 2035/0405* (2013.01)

(58) Field of Classification Search
   USPC ................................ 422/500, 501, 509, 547
   See application file for complete search history.

(56) References Cited

U.S. PATENT DOCUMENTS

| | | | |
|---|---|---|---|
| 6,080,364 A * | 6/2000 | Mimura et al. | 422/67 |
| 6,143,250 A | 11/2000 | Tajima | |
| 6,202,278 B1 | 3/2001 | Nakayama et al. | |
| 6,337,053 B1 | 1/2002 | Tajima | |
| 6,602,474 B1 | 8/2003 | Tajima | |
| 7,150,778 B1 * | 12/2006 | Dauber | B01D 53/02 55/340 |
| 8,220,228 B2 | 7/2012 | Itoh | |
| 2002/0046614 A1 | 4/2002 | Alley | |
| 2003/0070498 A1 * | 4/2003 | Ohyama et al. | 73/863.01 |
| 2006/0266766 A1 * | 11/2006 | Andrews | 222/14 |

FOREIGN PATENT DOCUMENTS

| | | |
|---|---|---|
| JP | 06-18530 A | 1/1994 |
| JP | 7-29464 U | 6/1995 |
| JP | 11-230967 A | 8/1999 |
| JP | 2000-146985 A | 5/2000 |
| JP | 2006-158335 A | 6/2006 |
| JP | 2008-279128 A | 11/2008 |
| JP | 2009-168734 A | 7/2009 |
| WO | 97/05492 A1 | 2/1997 |

* cited by examiner (a)

(b)

(a)

(b)

(c)

(g)

(h)

(i)

(a)

(b)

(c)

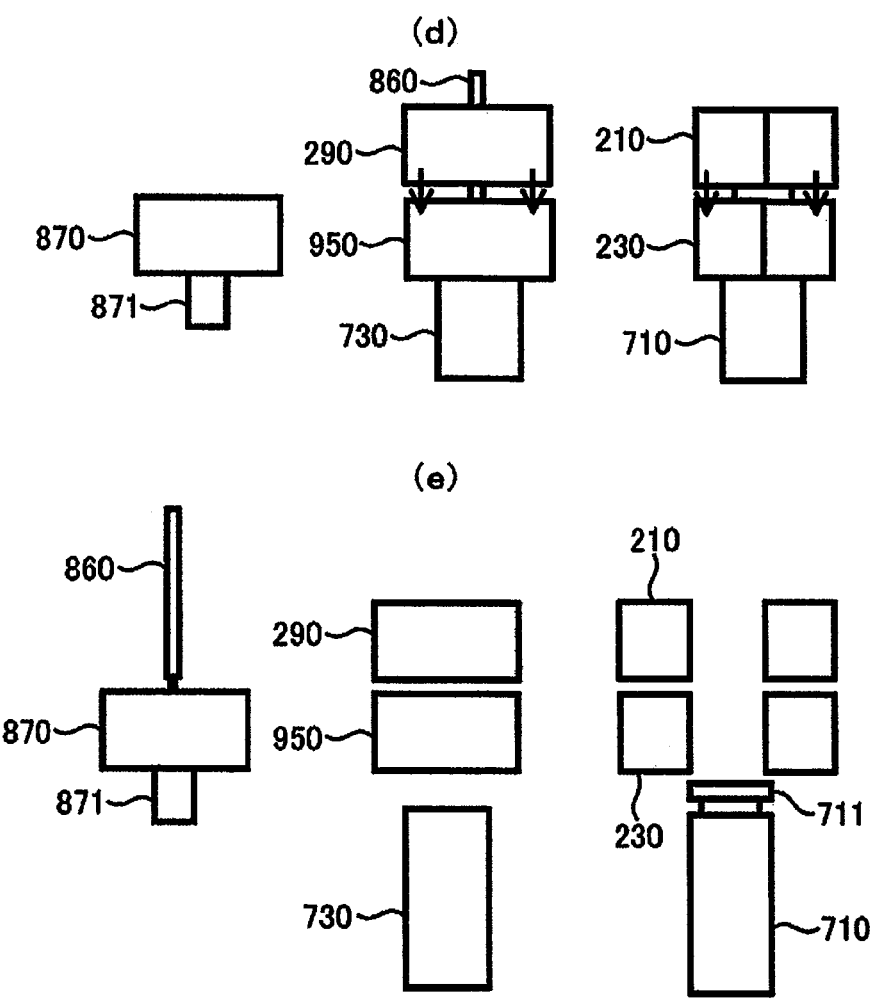

PLUG APPLICATION AND REMOVAL DEVICE AND SAMPLE PROCESSING DEVICE

TECHNICAL FIELD

The present invention relates to a plug application and removal device for removing a plug of a sample container and relates to a sample processing device.

BACKGROUND ART

As a background technique of the present technical field, Japanese Patent Application Laid-Open Publication No. 2008-279128 (Patent Document 1) is cited. This publication document describes to provide: a blood-collection-tube clamp mechanism that clamps a vacuum blood collection tube at a plug removing position in an upright state; a chuck mechanism that is provided to the plug removing position and that holds a plug body of the vacuum blood collection tube; sealing pressure-reducing means that are provided to the chuck mechanism, and that seal periphery of an opening of the vacuum blood collection tube including the plug body in holding the plug body of the vacuum blood collection tube, and besides, that reduce a pressure of this sealed region so as to be as the same as an internal pressure of the vacuum blood collection tube; and an ascending/descending mechanism that lifts the chuck mechanism from a plug-holding position to remove the plug body of the vacuum blood collection tube (see Abstract).

Moreover, Japanese Patent Application Laid-Open Publication No. H06-18530 (Patent Document 2) is cited. In this publication, a shape of a reaction disk is a disk shape, and a center part of the same is hollow. In the center part, a cylindrical sucking duct for sucking a gas from a peripheral edge part is arranged. Infectious aerosol generated in periphery of an analysis unit is sucked from many directions (in 360-degree directions) by an aerosol sucking duct, is removed through a pre-filter and a HEPA filter, and then, is discharged to outside. Also, the pre-filter can be easily detached from the sucking duct, and can be easily replaced. Therefore, this publication describes that an automatic analysis device that can prevent secondary infection of an operator and ensure safety is achieved with a simple configuration (see Abstract).

Also, Japanese Patent Application Laid-Open Publication No. H02-31165 (Patent Document 3) is cited. This publication describes that safety of an operator, appropriate dispensing, and protection of a device can be achieved by sucking a misty gas, which is generated upon liquid discharge, before spreading in a dispensing operation of various samples (see Abstract).

PRIOR ART DOCUMENTS

Patent Documents

PATENT DOCUMENT 1: Japanese Patent Application Laid-Open Publication No. 2008-279128
PATENT DOCUMENT 2: Japanese Patent Application Laid-Open Publication No. H06-18530
PATENT DOCUMENT 3: Japanese Patent Application Laid-Open Publication No. H02-31165

DISCLOSURE OF THE INVENTION

Problems to be Solved by the Invention

In the plug removing device according to the Patent Document 1, the vacuum blood collection tube is covered with a covering member, and an air in the space between the covering member and the vacuum blood collection tube is sucked under vacuum by a vacuum pump so as to reduce a pressure therein and to provide the pressure as the same as that inside the vacuum blood collection tube, and then, the plug body of the vacuum blood collection tube is detached. Therefore, in this plug removing device, there is no airflow in the space between the covering member and the vacuum blood collection tube after the plug body is detached, and therefore, there is a possibility that the blood remains in the space if the blood is spilled out of the vacuum blood collection tube to the space, and the blood is peripherally scattered when the covering member is opened. Note that the possibility of the blood spill out of the vacuum blood collection tube is considered in a case in which blood mist has been generated inside the vacuum blood collection tube during transportation, in a centrifugal separation step, etc., and in a case in which the blood is scattered when the plug body is detached with the blood being adhered thereto.

In the automatic analysis device described in the Patent Document 2, many reaction containers are arranged on an outer peripheral side of the rotating reaction disk, and the aerosol is sucked from the aerosol sucking duct provided at the center part of the reaction disk. That is, the aerosol generated in the vicinity of the reaction disk is sucked to the center part of the reaction disk, and is prevented from being scattered to the outer peripheral side of the reaction disk. However, the contamination in the circumferential direction of the reaction disk on which the many reaction containers are arranged, that is, the contamination between the adjacent reaction containers is not particularly taken into consideration. For example, when mist is scattered upon dispensing the sample to the reaction container, no particular measure is taken against a possibility of mixing to the adjacent reaction container.

In the automatic analysis device described in the Patent Document 3, the misty gas generated from a probe outlet can be sucked by providing a duct, which is gas sucking means, in the vicinity of a liquid-discharging part of a probe. However, only by the sucking from one direction, there is a possibility that the gas enters into an adjacent well depending on a size of the generated mist and a moving direction of the same.

The present invention provides a plug application and removal device that prevents the peripheral scattering of the mist which is generated upon removing a plug of a sample container. Alternatively, the present invention provides a sample processing device that prevents the mist, which is generated upon dispensing a sample to a container, from being mixed into another container.

Means for Solving the Problems

While the present application includes a plurality of means for solving the above-described problems, one example of them is cited as a plug removing device having: a container holding mechanism for holding a container in which a sample is filled and which is sealed with a plug; and a plug removing mechanism for removing the plug of the container, and the sample-container holding mechanism is provided with a sample control mechanism for controlling movement of liquid or mist spilled out of the container.

Desirably, the sample control mechanism is an air sucking mechanism, a partition, or both of them.

More desirably, the plug removing mechanism has a sample control mechanism for controlling movement of the sample spilled out of the container.

Alternatively, in a sample processing device having: an analysis-container holding mechanism for holding an analysis container to which a sample is dispensed from a sample container; and a dispensing mechanism guide for guiding a dispensing mechanism which dispenses the sample, airflow is generated between the dispensing mechanism guide and the analysis-container holding mechanism from the dispensing mechanism guide side toward the analysis-container holding mechanism side.

Alternatively, a sample processing device has: a sample dispenser for dispensing a sample from a sample container to an analysis container; and a container holding mechanism for holding and moving a plurality of the analysis containers, and the container holding mechanism moves the analysis container to a sample discharging position at which the sample is discharged by the dispenser. In the sample processing device, a partition is provided in an upper space between the sample container stopped at the sample discharging position and a sample container adjacent to the sample container.

Desirably, in the upper space of the sample container stopped at the sample discharging position, a sucking mechanism for sucking air in a space not blocked by the partition is provided.

Effects of the Invention

According to the present invention, even if mist of a sample or a reagent is generated upon removing a plug of a sample container or a reagent container, movement of the mist can be controlled, and therefore, the peripheral scattering of the mist can be prevented.

Alternatively, since the airflow is controlled between the dispensing mechanism and the analysis container, the mist generated upon dispensing of the sample to the container can be prevented from being mixed to another container.

Alternatively, since the partition or the airflow control mechanism is provided between the adjacent containers and in the periphery of the adjacent containers, contamination is not generated between the containers.

BRIEF DESCRIPTIONS OF THE DRAWINGS

FIG. 7B is operation explanatory diagrams of a sample processing unit according to an embodiment of the present invention;

BEST MODE FOR CARRYING OUT THE INVENTION

Hereinafter, embodiments will be explained by using drawings.

First Embodiment

In the present embodiment, an example of a sample processing device 10 that removes a plug of a sample container and dispenses a sample into an analysis container will be explained.

Figure 1:
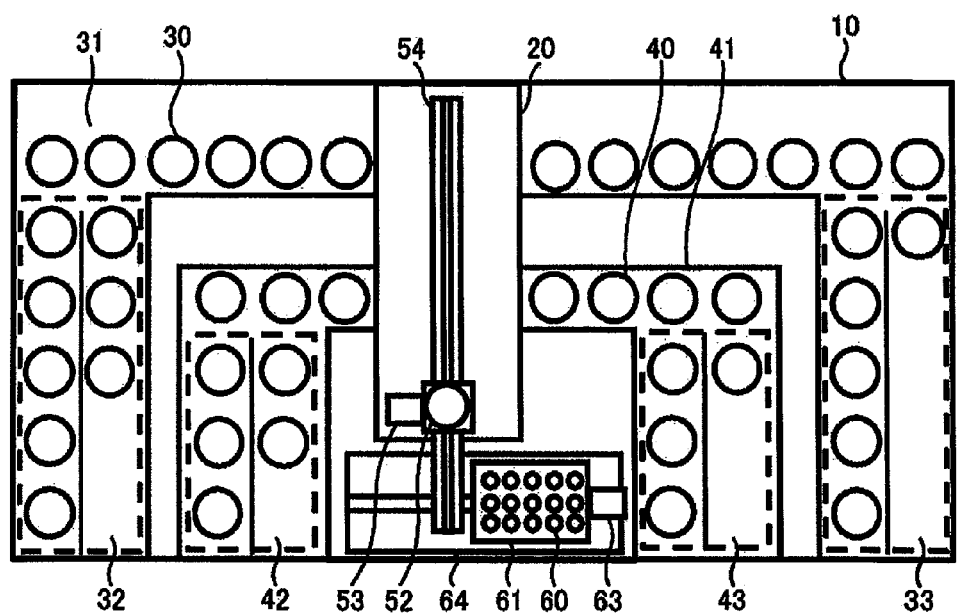
FIG. 1 is an example of a configuration diagram of a sample processing device.

FIG. 1 is a top view of a device in an example of the sample processing device of the present embodiment. Sample containers 30 are loaded into a sample-container loading unit 32, are conveyed by a sample-container conveying unit 31, pass through a sample processing unit 20, and are stored in a sample-container storing unit 33. A method of conveying the sample containers 30 include not only a method of directly conveying the sample containers but also a method conveying the sample containers in each rack or each holder on which one or a plurality of sample containers are mounted. Also, the method may be not only a linear method (a method of linearly moving the sample containers) illustrated in FIG. 1 but also a disk method (a method of moving the sample containers by a rotating operation) or others, and the method of conveying the sample containers is not limited to the present embodiment. Similarly, analysis containers 40 are loaded into an analysis-container loading unit 42, are conveyed by an analysis-container conveying unit 41, pass through the sample processing unit 20, and are stored in an analysis-container storing unit 43.

In the sample processing unit 20, a sample in the sample container is dispensed into the analysis container by a dispenser (50 of FIG. 4). The dispenser is moved along a dispenser guide 54 by a dispenser horizontal motor 53, and can be vertically moved by a dispenser vertical motor 52. Dispensing chips 60 are held by a dispensing-chip holding unit 61, and are moved along a dispensing-chip-holding-unit guide 64 by a dispensing-chip-holding-unit horizontal motor 63. A method of driving the dispenser is not limited to this method, and the dispenser may dispense the sample from the sample container to the analysis container by rotationally moving around an axis.

Figure 2:
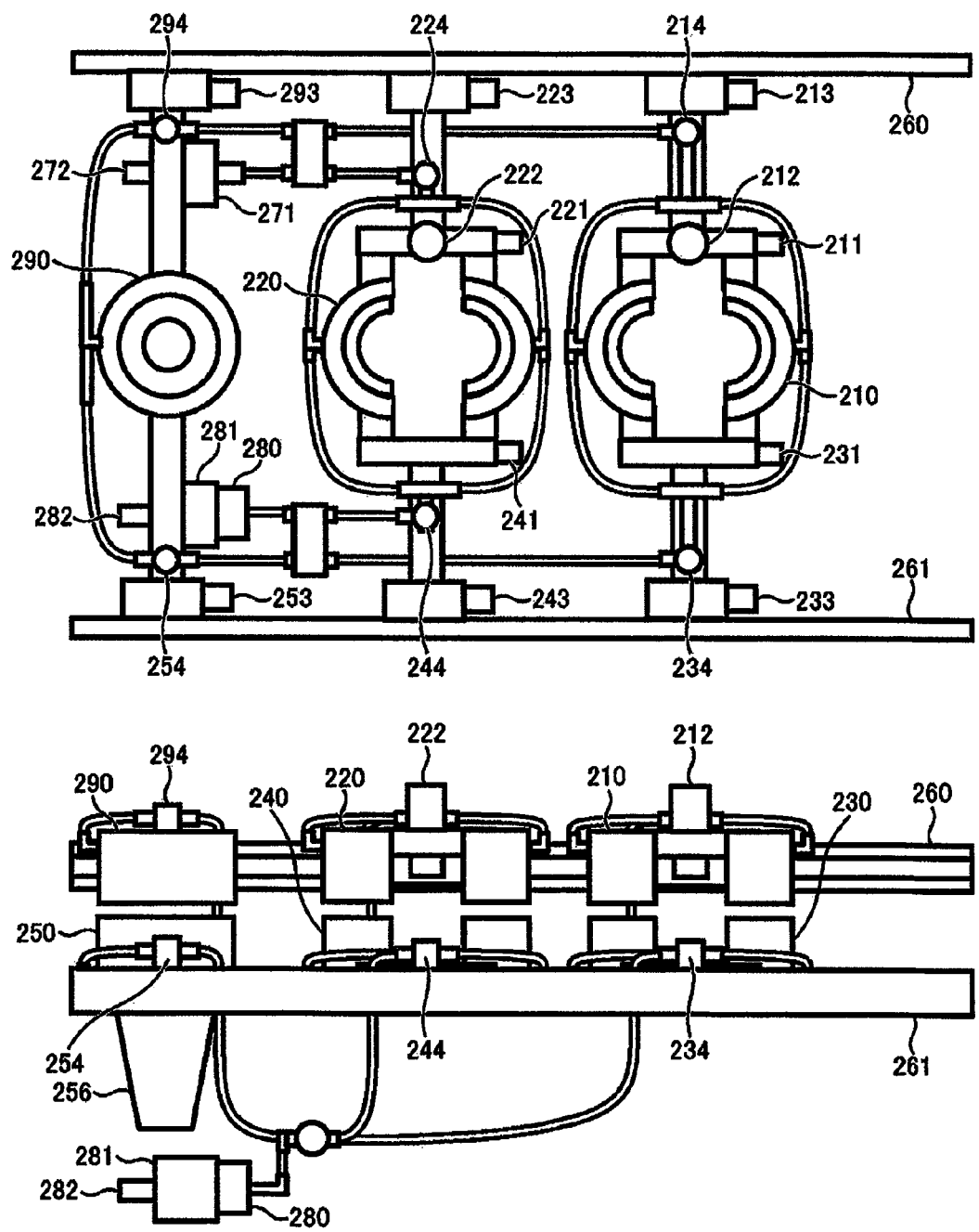
FIG. 2 is detailed diagrams of a sample processing unit according to an embodiment of the present invention, viewed from above and side.

FIG. 2 is detailed diagrams of the sample processing unit, and an upper diagram is a top view and a lower diagram is a side view.

A first plug-removing and discharging mechanism 210 can be opened/closed by a first plug-removing-and-discharging-mechanism opening/closing motor 211, can be vertically moved by a first plug-removing-and-discharging-mechanism vertical motor 212, and can be moved in a horizontal direction along a discharging mechanism guide 260 by a first plug-removing-and-discharging-mechanism horizontal motor 213.

A second plug-removing and discharging mechanism 220 can be opened/closed by a second plug-removing-and-discharging-mechanism opening/closing motor 221, can be vertically moved by a second plug-removing-and-discharging-mechanism vertical motor 222, and can be moved in a horizontal direction along the discharging mechanism guide 260 by a second plug-removing-and-discharging-mechanism horizontal motor 223.

A discharging mechanism 290 can be moved in the horizontal direction along the discharging mechanism guide 260 by a discharging-mechanism horizontal motor 293.

A sample-container holding and sucking mechanism 230 can be opened/closed by a sample-container-holding-and-sucking-mechanism opening/closing motor 231 and can be moved in the horizontal direction along a sucking mechanism guide 261 by a sample-container-holding-and-sucking-mechanism horizontal motor 233.

An analysis-container holding and sucking mechanism 240 can be opened/closed by an analysis-container-holding-and-sucking-mechanism opening/closing motor 241, and can be moved in the horizontal direction along the sucking mechanism guide 261 by an analysis-container-holding-and-sucking-mechanism horizontal motor 243.

A dispensing-chip disposing and sucking mechanism 250 can be moved in the horizontal direction along the sucking mechanism guide 261 by a dispensing-chip-disposing-and-sucking-mechanism horizontal motor 253.

Figure 3:
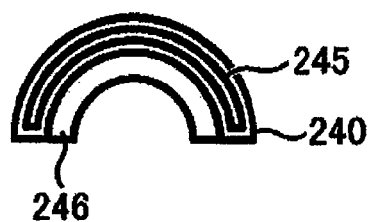
FIG. 3 is detailed diagrams of an analysis-container holding and sucking mechanism and a dispensing-chip disposing and sucking mechanism.
Figure 3:
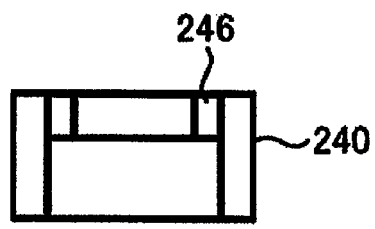
Figure 3:
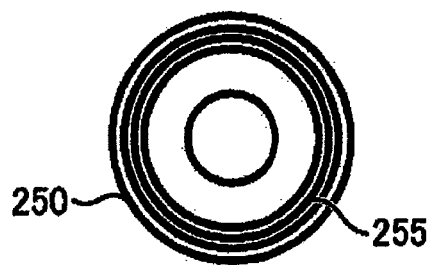
Figure 3:
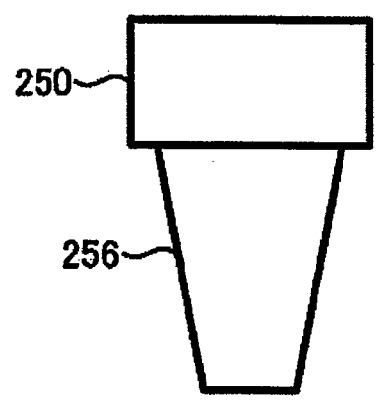

An item (a) of FIG. 3 illustrates the analysis-container holding and sucking mechanism 240, and an item (b) of FIG. 3 illustrates details of the dispensing-chip disposing and sucking mechanism 250. An upper diagram is a top view, and a lower diagram is a side view.

The analysis-container holding and sucking mechanism 240 is provided with sucking units 245 and holding units 246. A pair of the two holding units 246 holds the analysis container. The sucking units 245 have a structure for sucking air, each one of the sucking units is semicircular, and a combination of two of them is substantially circular. The structure is for generating uniform sucked airflow in periphery of the opening of the analysis container when the analysis container is held by the holding unit 246.

The sample-container holding and sucking mechanism 230 has the substantially same structure as that of the analysis-container holding and sucking mechanism 240, and sucks air by a sucking unit (not illustrated) in the sample container. They are semicircular as well as the sucking units 245 of the analysis-container holding and sucking mechanism 240, and generate uniform sucked airflow in periphery of the opening of the sample container.

The first plug-removing and discharging mechanism 210 and the second plug-removing and discharging mechanism 220 have structures obtained by vertically reversing the analysis-container holding and sucking mechanism 240, and are provided with a discharging unit of the first plug-removing and discharging mechanism and a discharging unit of the second plug-removing and discharging mechanism at positions facing the sucking unit of the sample container and the sucking unit of the analysis container so as to discharge the air, respectively. More specifically, the respective discharging units are semicircular, and two of them are combined to be circular, and generate uniform discharged airflow in periphery of the plug.

The dispensing-chip disposing and sucking mechanism 250 is provided with a sucking unit 255 and a dispensing-chip disposing container 256. The dispensing-chip disposing container 256 has a structure for disposing the dispensing chip 60, which has been used for the sample dispensing. The dispensing-chip-disposing-and-sucking-mechanism sucking unit 255 has a structure for sucking air, and is circular. This is a structure for generating uniform sucked airflow in periphery of an opening of the dispensing-chip disposing container 256.

The discharging mechanism 290 is provided with a circular discharging unit at a position facing the sucking unit 255 of the dispensing-chip disposing and sucking mechanism 250. This is a structure for generating uniform discharged airflow in periphery of the dispenser 50.

When any of a first plug-removing-and-discharging-mechanism discharging valve 214, a second plug-removing-and-discharging-mechanism discharging valve 224, and a discharging-mechanism discharging valve 294 is opened during operation of a discharging fan 271 (FIG. 2), air outside the device is sucked from a sucking duct 272 and is discharged from the discharging unit of each mechanism.

When any of a sample-container-holding-and-sucking-mechanism sucking valve 234, an analysis-container-holding-and-sucking-mechanism sucking valve 244, and a dispensing-chip-disposing-and-sucking-mechanism sucking valve 254 is opened during operation of an air-discharge fan 281, the air is sucked from the sucking unit of each mechanism, passes through an air-discharge filter 280, and is discharged from an air-discharge duct 282 to outside of the device.

FIGS. 4A to 4D illustrate operations of the sample processing unit according to the first embodiment of the present invention. The present embodiment describes a case in which the second plug-removing and discharging mechanism 220 (FIG. 2) is not used, and the second plug-removing and discharging mechanism 220 is omitted. The drawings illustrate side views of the sample processing unit, and each discharging mechanism, the valves of the sucking mechanisms, the motors, air pipes, guides, etc. are omitted.

Figure 4A:
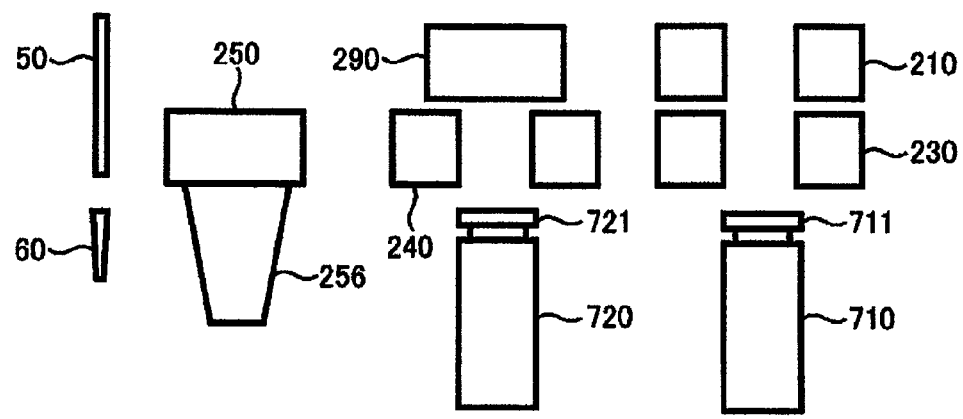
FIG. 4A is operation explanatory diagrams of the sample processing unit according to an embodiment of the present invention.
Figure 4A:
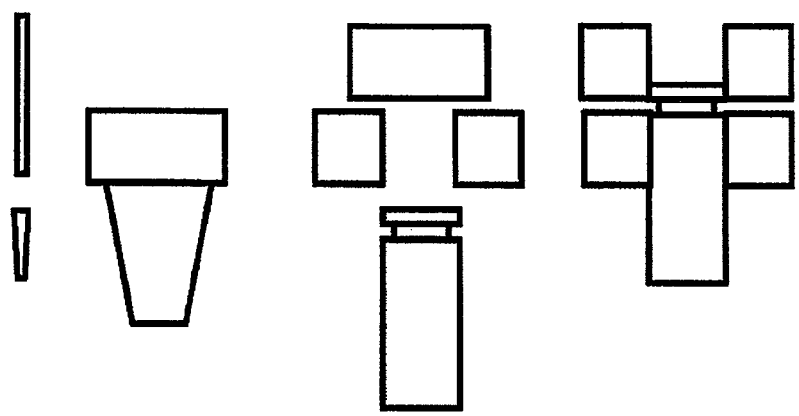
Figure 4A:
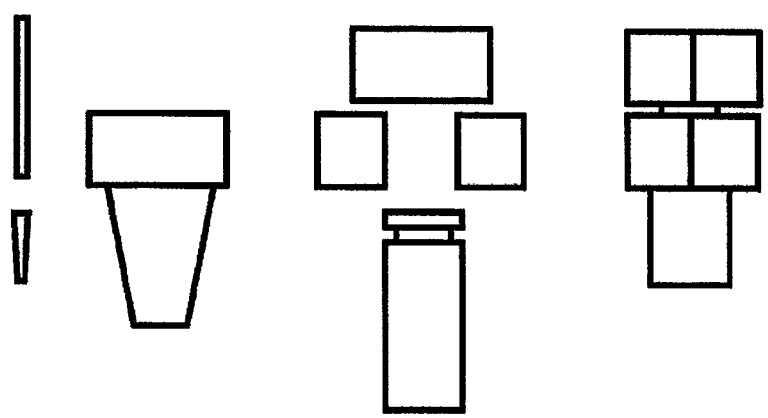

An item (a) of FIG. 4A illustrates such an initial state that a sample-container main body 710 with being sealed by a sample container plug 711 is set below the plug-removing and discharging mechanism 210 and the sample-container holding and sucking mechanism 230 each of which is in an open state. An analysis-container main body 720 with being sealed by an analysis container plug 721 is set below the discharging mechanism 290 and the analysis-container holding and sucking mechanism 240 which is in an open state. The dispenser 50 is positioned beside the dispensing-chip disposing and sucking mechanism 250 in a standby state, and the dispensing chip 60 is positioned below the dispenser 50.

The sample-container main body 710 is moved up (an item (b) of FIG. 4A) by an ascending/descending mechanism (not illustrated) which positions the sample container at the plug-removing and discharging mechanism 210. The sample container plug 711 is moved up to and is stopped at a height of the plug-removing and discharging mechanism 210.

The plug-removing-and-discharging-mechanism opening/closing motor 211 and the sample-container-holding-and-sucking-mechanism opening/closing motor 231 illustrated in FIG. 2 are operated to close the plug-removing and discharging mechanism 210 and the sample-container holding and sucking mechanism 230, so that the sample container plug 711 and the sample-container main body 710 are held, respectively (an item(c) of FIG. 4A).

Figure 4B:
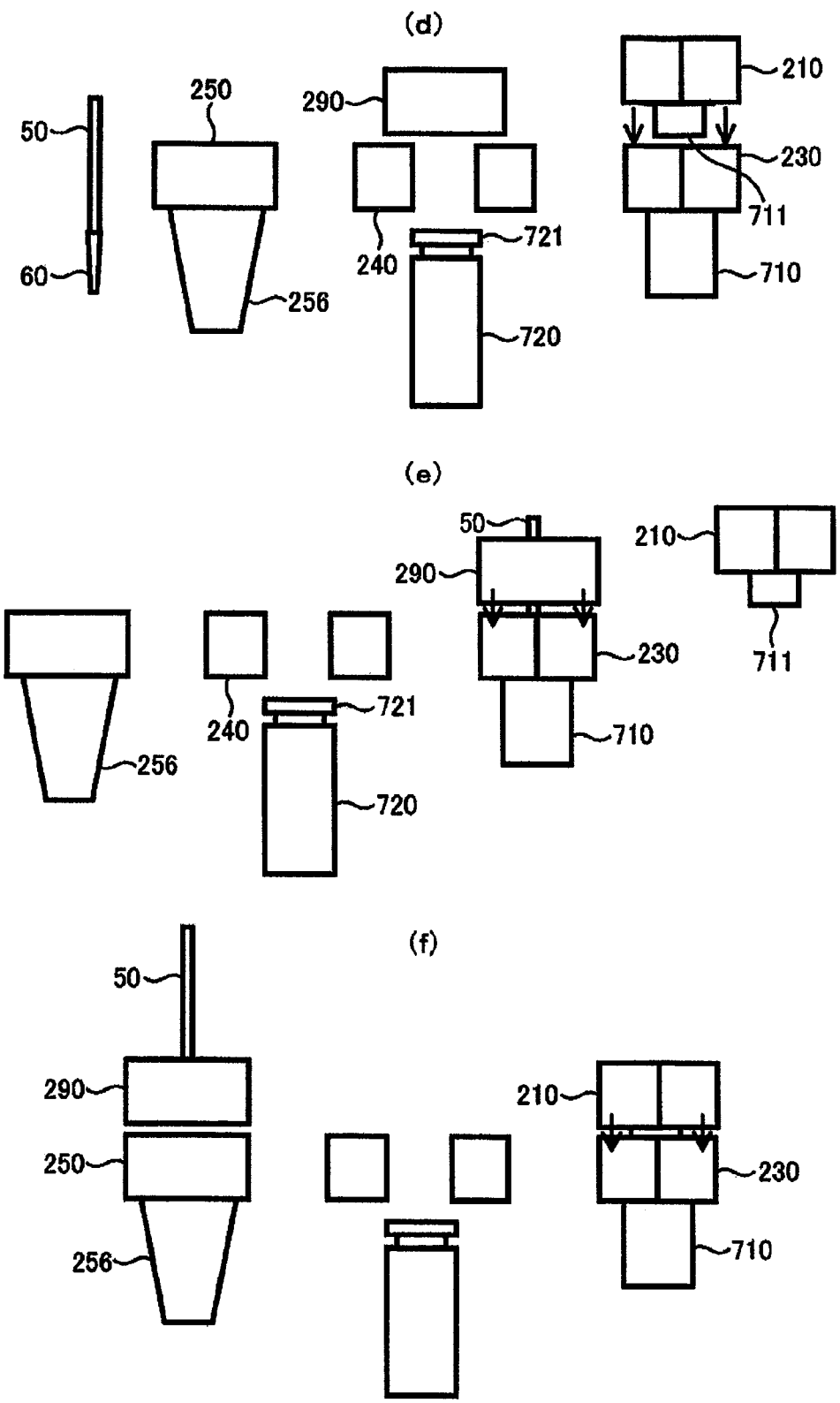
FIG. 4B is operation explanatory diagrams of the sample processing unit according to an embodiment of the present invention.

While the plug-removing-and-discharging-mechanism discharging valve 214 and the sample-container-holding-and-sucking-mechanism sucking valve 234 are opened to discharge the air from the discharging unit of the plug-removing and discharging mechanism 210 and to suck the air (illustrated with arrows of an item of (d) of FIG. 4B) by the suck unit of the sample-container holding and sucking mechanism 230, the plug-removing-and-discharging-mechanism vertical motor 212 is operated so as to lift the plug-removing and discharging mechanism 210 and remove the sample container plug 711 (the item of (d) of FIG. 4B). At the same time, by operating the dispenser vertical motor 52 (FIG. 1), the dispenser 50 is moved down so as to attach the dispensing chip 60 to the dispenser 50.

Even if the mist of the sample is generated by a pressure difference between inside and outside of the sample container or others when the sample container plug 711 is removed, airflow that surrounds the plug and the opening of the sample container are formed between the plug-removing and discharging mechanism 210 and the sample-container holding and sucking mechanism 230, and therefore, the mist is sucked from the sucking unit (not illustrated) of the sample-container holding and sucking mechanism without being peripherally scattered. Therefore, there is no concern for the contamination.

Next, the plug-removing-and-discharging-mechanism discharging valve 214 and the sample-container-holding-and-sucking-mechanism sucking valve 234 are once closed to stop the airflow between the plug-removing and discharging mechanism 210 and the sample-container holding and sucking mechanism 230. The plug-removing and discharging mechanism 210 and the discharging mechanism 290 are moved along the discharging mechanism guide 260 by operating the plug-removing-and-discharging-mechanism horizontal motor 213 and the discharging-mechanism horizontal motor 293 so that the discharging mechanism 290 is stopped immediately above the sample-container holding and sucking mechanism 230, i.e., immediately above the plug-removed sample-container main body 710.

The dispenser 50 is inserted into the sample-container main body 710, and sucks the sample (an item (e) of FIG. 4B) while the airflow is generated from the discharging mechanism 290 to the sample-container holding and sucking mechanism 230 (illustrated with arrows of the item (e) of FIG. 4B) by opening the discharging-mechanism discharging valve 294 and the sample-container-holding-and-sucking-mechanism sucking valve 234.

Even if the mist is generated upon the sample sucking, the airflow surrounding the dispenser and the opening of the sample container is formed between the discharging mechanism 290 and the sample-container holding and sucking mechanism 230, and therefore, the mist is sucked from the sucking unit of the sample-container holding and sucking mechanism without being peripherally scattered. Therefore, there is no concern for the contamination.

When the sucking of the sample is completed, the dispenser 50 is moved up, and the airflow is once stopped. The plug-removing and discharging mechanism 210 and the discharging mechanism 290 are moved along the discharging mechanism guide 260 by operating the plug-removing-and-discharging-mechanism horizontal motor 213 and the discharging-mechanism horizontal motor 293 so that the discharging mechanism 290 is moved immediately above the dispensing-chip disposing and sucking mechanism 250, and so that the plug-removing and discharging mechanism 210 is moved immediately above the sample-container holding and sucking mechanism 230.

The plug-removing-and-discharging-mechanism vertical motor 212 is operated while the plug-removing-and-discharging-mechanism discharging valve 214 and the sample-container-holding-and-sucking-mechanism sucking valve 234 are opened to discharge the air by the plug-removing and discharging mechanism 210 and to suck the air by the sample-container holding and sucking mechanism 230, so that the plug-removing and discharging mechanism 210 is moved down to apply the sample container plug 711 to the sample-container main body 710 (an item (f) of FIG. 4B).

Even if the mist is generated upon the plug application, the airflow surrounding the plug and the opening of the sample container is formed between the plug-removing and discharging mechanism 210 and the sample-container holding and sucking mechanism 230, and therefore, the mist is sucked from the sucking unit of the sample-container holding and sucking mechanism without being peripherally scattered. Therefore, there is no concern for the contamination.

Figure 4C:
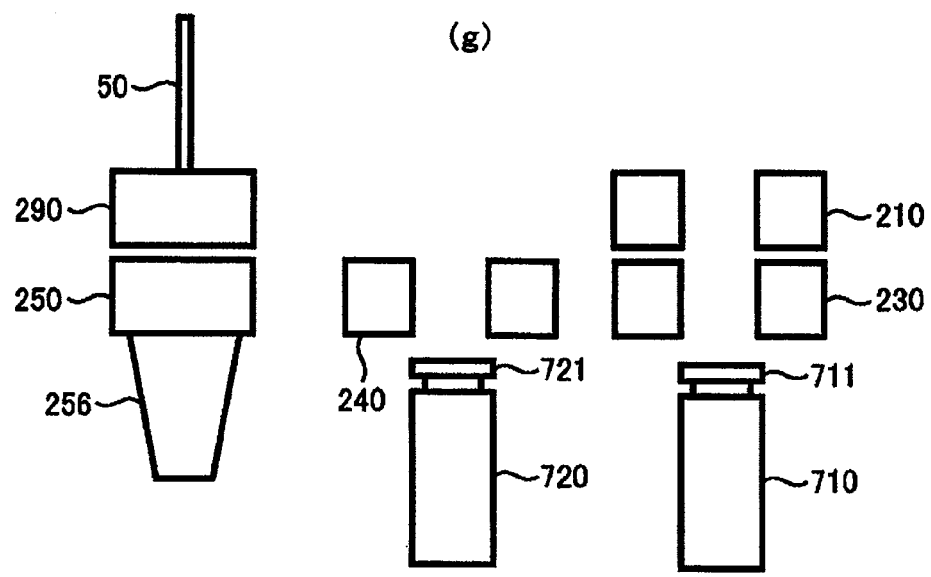
FIG. 4C is operation explanatory diagrams of the sample processing unit according to an embodiment of the present invention.
Figure 4C:
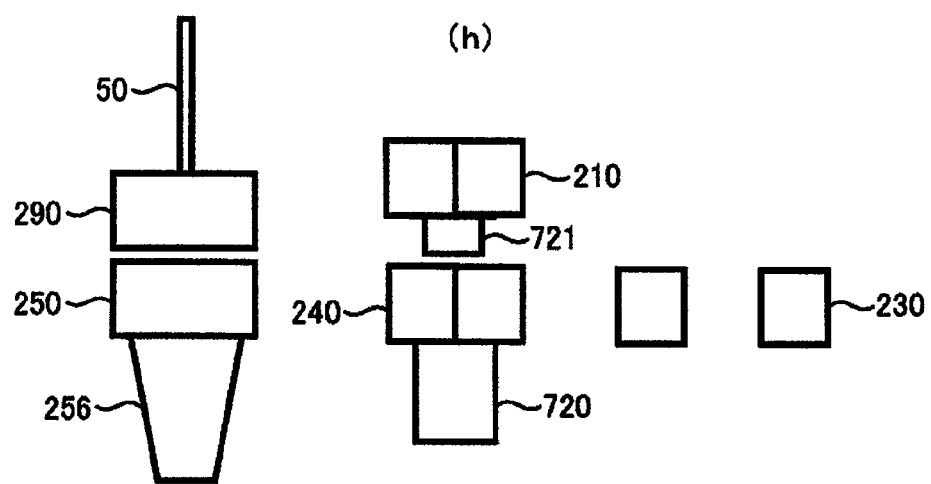
Figure 4C:
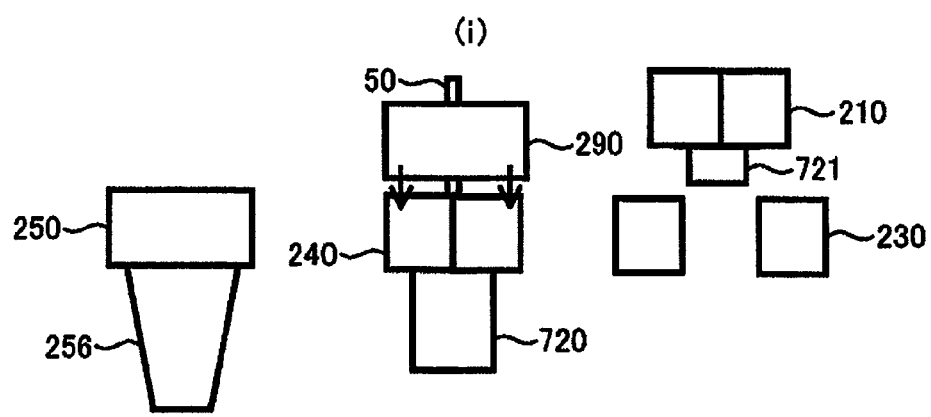

The plug-removing and discharging mechanism 210 and the sample-container holding and sucking mechanism 230 are opened by operating the plug-removing-and-discharging-mechanism opening/closing motor 211 and the sample-container-holding-and-sucking-mechanism opening/closing motor 231, so that the sample-container main body 710 is moved down (an item (g) of FIG. 4C). The sample-container main body 710 is conveyed to the sample-container storing unit 33 by the sample-container conveying unit 31.

Next, the plug-removing and discharging mechanism 210 is moved along the discharging mechanism guide 260 by operating the plug-removing-and-discharging-mechanism horizontal motor 213, so as to stop immediately above the analysis-container holding and sucking mechanism 240. The analysis-container main body 720 with the analysis container plug 721 being applied thereto is set below the analysis-container holding and sucking mechanism 240.

The analysis-container main body 720 is moved up by an ascending/descending mechanism (not illustrated) which positions the analysis container at the plug-removing and discharging mechanism 210, and the plug-removing and discharging mechanism 210 and the analysis-container holding and sucking mechanism 240 are closed by operating the plug-removing-and-discharging-mechanism opening/closing motor 211 and the analysis-container-holding-and-sucking-mechanism opening/closing motor 241, so that the analysis container plug 721 and the analysis-container main body 720 are held, respectively. The plug-removing and discharging mechanism 210 is moved up by operating the plug-removing-and-discharging-mechanism vertical motor 212 so as to remove the analysis container plug 721 (an item (h) of FIG. 4C).

The plug-removing and discharging mechanism 210 and the discharging mechanism 290 are moved along the discharging mechanism guide 260 by operating the plug-removing-and-discharging-mechanism horizontal motor 213 and the discharging-mechanism horizontal motor 293 so that the discharging mechanism 290 is stopped immediately above the analysis-container holding and sucking mechanism 240, in other words, immediately above the plug-removed analysis-container main body 720. the dispenser 50 is inserted in the analysis-container main body 720 to discharge the sample (an item (i) of FIG. 4C) while the discharging-mechanism discharging valve 294 and the analysis-container-holding-and-sucking-mechanism sucking valve 244 are opened to generate the airflow from the discharging mechanism 290 to the analysis-container holding and sucking mechanism 240 (illustrated with arrows of the item (i) of FIG. 4C).

Even if the mist is generated upon the sample discharge, the airflow surrounding the dispenser and the opening of the analysis container is formed between the discharging mechanism 290 and the analysis-container holding and sucking mechanism 240, and therefore, the mist is sucked from the sucking unit of the analysis-container holding and sucking mechanism without being peripherally scattered. Therefore, there is no concern for the contamination.

When the discharging of the sample is completed, the dispenser 50 is moved up so that the airflow is once stopped. The plug-removing and discharging mechanism 210 and the discharging mechanism 290 are moved along the discharging mechanism guide 260 by operating the plug-removing-and-discharging-mechanism horizontal motor 213 and the discharging-mechanism horizontal motor 293, so that the discharging mechanism 290 is moved to a position immediately above the dispensing-chip disposing and sucking mechanism 250, and so that the plug-removing and discharging mechanism 210 is moved to a position immediately above the analysis-container holding and sucking mechanism 240.

Figure 4D:
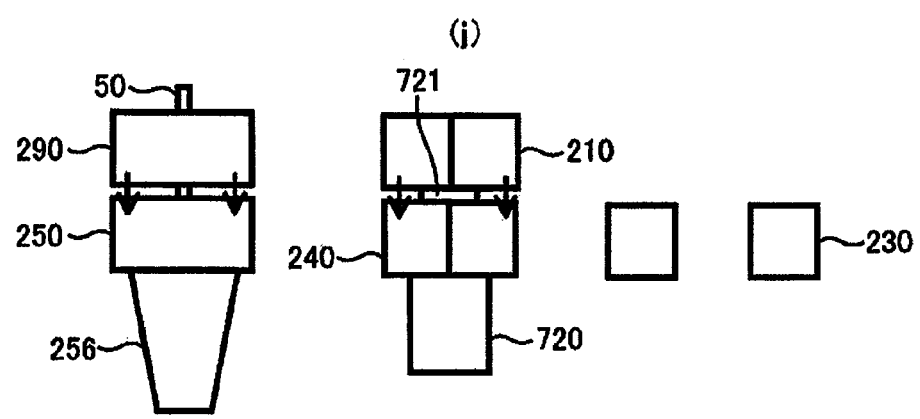
FIG. 4D is an operation explanatory diagram of the sample processing unit according to an embodiment of the present invention.

The plug-removing-and-discharging-mechanism vertical motor 212 is operated while opening the plug-removing-and-discharging-mechanism discharging valve 214 and the analysis-container-holding-and-sucking-mechanism sucking valve 244 so as to discharge the air by the plug-removing and discharging mechanism 210 and so as to suck the air by the analysis-container holding and sucking mechanism 240, so that the plug-removing and discharging mechanism 210 is moved down to apply the analysis container plug 721 to the analysis-container main body 720 (an item (j) of FIG. 4D).

Even if the mist is generated upon the plug application, the airflow surrounding the plug and the opening of the analysis container is formed between the plug-removing and discharging mechanism 210 and the analysis-container holding and sucking mechanism 240, and therefore, the mist is sucked from the sucking unit of the analysis-container holding and sucking mechanism without being peripherally scattered. Therefore, there is no concern for the contamination.

At the same time, the dispenser 50 disposes the dispensing chip 60 to the dispensing-chip disposing container 256 while opening the discharging-mechanism discharging valve 294 and the dispensing-chip-disposing-and-sucking-mechanism sucking valve 254 so as to discharge the air by the discharging mechanism 290 and so as to suck the air by the dispensing-chip disposing and sucking mechanism 250.

Even if the mist is generated upon the disposing of the dispensing chip, the airflow surrounding the dispenser and the opening of the dispensing-chip disposing container is formed between the discharging mechanism 290 and the dispensing-chip disposing and sucking mechanism 250, and therefore, the mist is sucked from the sucking unit of the dispensing-chip disposing and sucking mechanism without being peripherally scattered. Therefore, there is no concern for the contamination.

The plug-removing and discharging mechanism 210 and the analysis-container holding and sucking mechanism 240 are opened by operating the plug-removing-and-discharging-mechanism opening/closing motor 211 and the analysis-container-holding-and-sucking-mechanism opening/closing motor 241 with stopping the entire airflow, so that the analysis-container main body 720 is moved down. The analysis-container main body 720 is conveyed to the analysis-container storing unit 43 by the analysis-container conveying unit 41.

Next, the dispenser 50 is moved up and returns to the initial state. The plug-removing and discharging mechanism 210 and the discharging mechanism 290 also return to the initial state, and process the next sample container (an item (a) of FIG. 4A).

In the present embodiment, the airflow is controlled so that the samples are not peripherally scattered upon the plug removal (an item (d) of FIG. 4B) of the sample-container main body 710 and the plug application (an item (f) of FIG. 4B) of the same, upon the sample sucking (an item (e) of FIG. 4B) from the sample-container main body 710, upon the sample discharge (an item (i) of FIG. 4C) to the analysis-container main body 720, upon the plug application of the analysis-container main body 720, and upon the disposal (an item (j) of FIG. 4D) of the dispensing chip 60 to the dispensing-chip disposing container 256 of the dispenser 50.

The airflow may be controlled at not only the timing described in the present embodiment but also any timing. For example, by controlling the airflow so as to flow from the discharging mechanism 290 to the dispensing-chip disposing and sucking mechanism 250 at such timing that the dispenser 50 is positioned immediately above the dispensing-chip disposing and sucking mechanism 250 as illustrated in the item (f) of FIG. 4B, the sample is not peripherally scattered even when the sample during the suction into the dispenser 50 and the dispensing chip 60 is spilled out since the airflow is peripherally controlled so as to suck the sample from the sucking unit of the dispensing-chip disposing and sucking mechanism.

Also, the discharged air volume and the sucked air volume can be adjusted by a discharging fan 271, an exhaust fan 281, and the respective valves (214, 224, 234, 244, 254, and 294). For example, if not only the discharged air but also the peripheral air are sucked by increasing the sucked air volume more than the discharged air volume, the misty sample generated from the dispensing chip 60 can be prevented from being spilled out to an upper part of the discharging mechanism 290 upon, for example, the disposal of the dispensing chip 60 (an item (j) of FIG. 4D) to the dispensing-chip disposing container 256.

Alternatively, not the discharging but only the sucking may be performed. For example, even if the mist of the sample is generated by, for example, a pressure difference between inside and outside of the sample container or others upon the plug removal of the sample container plug 711 illustrated in an item (d) of FIG. 4B, the sucked airflow surrounding the plug and the opening of the sample container is formed between the plug-removing and discharging mechanism 210 and the sample-container holding and sucking mechanism 230 by sucking the sample from the sucking unit of the sample-container holding and sucking mechanism 230, and the air is sucked from an outer peripheral part of a part between the plug-removing and discharging mechanism 210 and the sample-container holding and sucking mechanism 230 into an inner peripheral side thereof, and therefore, the mist is sucked from the sucking unit of the sample-container holding and sucking mechanism without being peripherally scattered. Therefore, there is no concern for the contamination.

Second Embodiment

In the present embodiment, an example of a device in which the sample can be processed while the dispenser in the sample sucking state or the plug in the removal state is stopped will be explained.

Figure 5A:
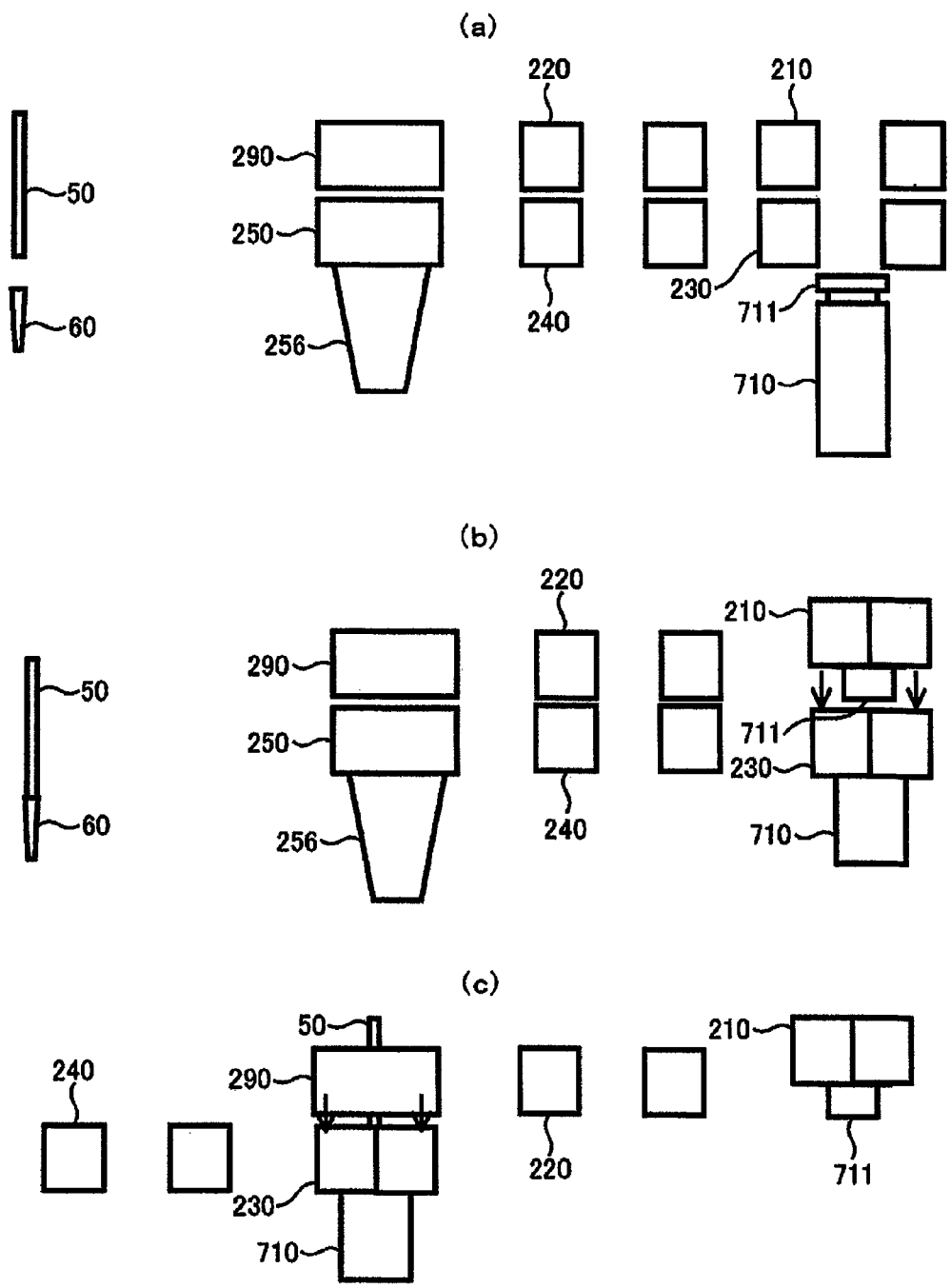
FIG. 5A is operation explanatory diagrams of the sample processing unit according to an embodiment of the present invention.
Figure 5B:
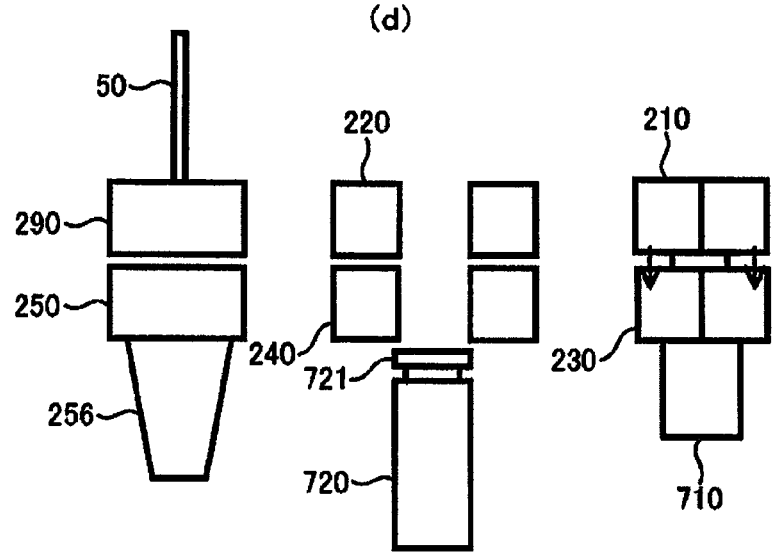
FIG. 5B is operation explanatory diagrams of the sample processing unit according to an embodiment of the present invention.
Figure 5B:
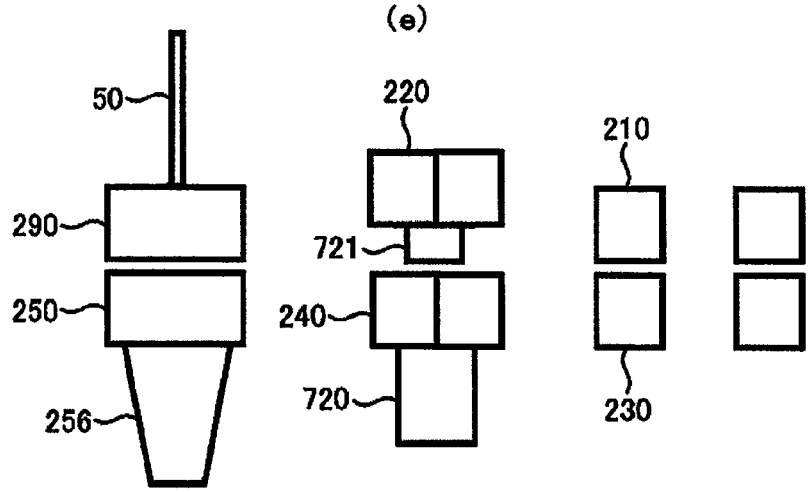
Figure 5B:
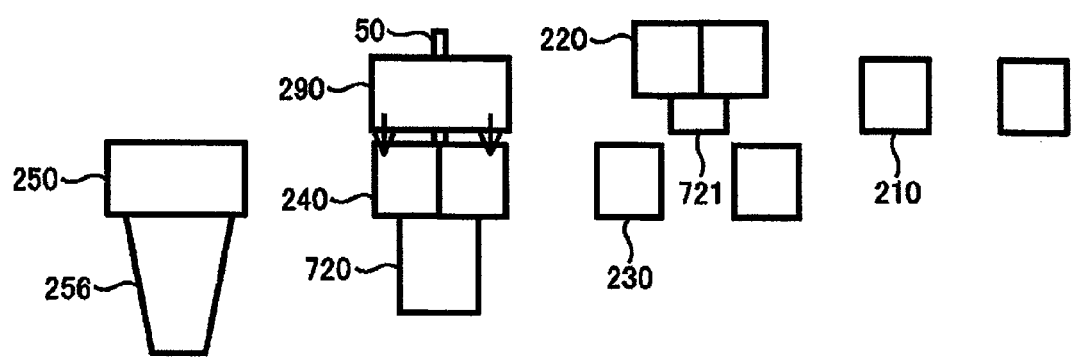
Figure 5C:
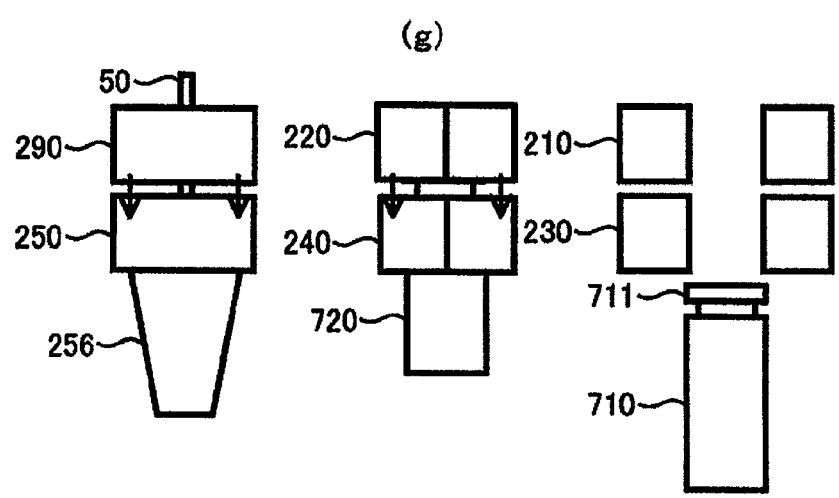
FIG. 5C is an operation explanatory diagram of the sample processing unit according to an embodiment of the present invention.

FIGS. 5A to 5C illustrate operations of a sample processing unit according to a second embodiment of the present invention. In the embodiment of FIG. 4, although the second plug-removing and discharging mechanism 220 in the configuration illustrated in FIG. 2 is not used, a second plug-removing and discharging mechanism 220 is used in the present embodiment. Similarly to the first embodiment, the drawings illustrate side views of the sample processing unit, and each of the discharging mechanisms, the valves of the sucking mechanisms, the motors, the air pipes, the guides, etc. is omitted.

An item (a) of FIG. 5A illustrates an initial state in which each of the first plug-removing and discharging mechanism 210, the second plug-removing and discharging mechanism 220, the sample-container holding and sucking mechanism 230, and the analysis-container holding and sucking mechanism 240 is opened, and in which the sample-container main body 710 with being sealed by the sample container plug 711 is set below the sample-container holding and sucking mechanism 230. The dispenser 50 is positioned beside the dispensing-chip disposing and sucking mechanism in a standby state, and the dispensing chip 60 is below the dispenser 50.

Similarly to the first embodiment, the sample-container main body 710 is moved up. The first plug-removing and discharging mechanism 210 and the sample-container holding and sucking mechanism 230 are closed by operating the first plug-removing-and-discharging-mechanism opening/closing motor 211 and the sample-container-holding-and-sucking-mechanism opening/closing motor 231 illustrated in FIG. 2, so that the sample container plug 711 and the sample-container main body 710 are held, respectively.

The first plug-removing-and-discharging-mechanism vertical motor 212 is operated while opening the first plug-removing-and-discharging-mechanism discharging valve 214 and the sample-container-holding-and-sucking-mechanism sucking valve 234 so as to discharge the air by the first plug-removing and discharging mechanism 210 and so as to suck the air by the sample-container holding and sucking mechanism 230, so that the first plug-removing and discharging mechanism 210 is moved up so as to remove the sample container plug 711 (an item (b) of FIG. 5A). At the same time, by operating the dispenser vertical motor 52, the dispenser 50 is moved down so as to attach the dispenser chip 60 to the dispenser 50.

Next, the first plug-removing-and-discharging-mechanism discharging valve 214 and the sample-container-holding-and-sucking-mechanism sucking valve 234 are once closed, so that the airflow between the first plug-removing and discharging mechanism 210 and the sample-container holding and sucking mechanism 230 is stopped.

The sample-container holding and sucking mechanism 230, the analysis-container holding and sucking mechanism 240, and the dispensing-chip disposing and sucking mechanism 250 are moved along the sucking mechanism guide 261 by operating the sample-container-holding-and-sucking-mechanism horizontal motor 233, the analysis-container-holding-and-sucking-mechanism horizontal motor 243, and the dispensing-chip-disposing-and-sucking-mechanism horizontal motor 253, so that the sample-container holding and sucking mechanism 230 is positioned below the discharging mechanism 290.

The dispenser 50 is inserted into the sample-container main body 710 to suck the sample (an item (c) of FIG. 5A) while opening the discharging-mechanism discharging valve 294 and the sample-container-holding-and-sucking-mechanism sucking valve 234 so as to generate the airflow from the discharging mechanism 290 to the sample-container holding and sucking mechanism 230. In the item (c) of FIG. 5A, the dispensing-chip disposing and sucking mechanism 250 is omitted.

When the sucking of the sample is completed, the dispenser 50 is moved up so that the airflow is once stopped. The sample-container holding and sucking mechanism 230, the analysis-container holding and sucking mechanism 240, and the dispensing-chip disposing and sucking mechanism 250 are moved along the sucking mechanism guide 261 by operating the sample-container-holding-and-sucking-mechanism horizontal motor 233, the analysis-container-holding-and-sucking-mechanism horizontal motor 243, and the dispensing-chip-disposing-and-sucking-mechanism horizontal motor 253, so that the sample-container holding and sucking mechanism 230 is positioned below the first plug-removing and discharging mechanism 210.

The first plug-removing and discharging mechanism 210 is moved down by operating the first plug-removing-and-discharging-mechanism vertical motor 212 while opening the first plug-removing-and-discharging-mechanism discharging valve 214 and the sample-container-holding-and-sucking-mechanism sucking valve 234 so as to discharge the air by the first plug-removing and discharging mechanism 210 and so as to suck the air by the sample-container holding and sucking mechanism 230, so that the sample container plug 711 is applied to the sample-container main body 710 (an item (d) of FIG. 5B).

At the same time, the analysis-container main body 720 sealed by the analysis container plug 721 is set below the analysis-container holding and sucking mechanism 240.

The first plug-removing and discharging mechanism 210 and the sample-container holding and sucking mechanism 230 are opened by operating the first plug-removing-and-discharging-mechanism opening/closing motor 211 and the sample-container-holding-and-sucking-mechanism opening/closing motor 231, so that the sample-container main body 710 is moved down.

The sample-container main body 710 is conveyed to the sample-container storing unit 33 by the sample-container conveying unit 31. At the same time, the analysis-container main body 720 is moved up, and the second plug-removing and discharging mechanism 220 and the analysis-container holding and sucking mechanism 240 are closed by operating the second plug-removing-and-discharging-mechanism opening/closing motor 221 and the analysis-container-holding-and-sucking-mechanism opening/closing motor 241, so that the analysis container plug 721 and the analysis-container main body 720 are held, respectively.

The second plug-removing and discharging mechanism 220 is moved up by operating the second plug-removing-and-discharging-mechanism vertical motor 222, so that the analysis container plug 721 is removed (an item (e) of FIG. 5B).

The sample-container holding and sucking mechanism 230, the analysis-container holding and sucking mechanism 240, and the dispensing-chip disposing and sucking mechanism 250 are moved along the sucking mechanism guide 261 by operating the sample-container-holding-and-sucking-mechanism horizontal motor 233, the analysis-container-holding-and-sucking-mechanism horizontal motor 243, and the dispensing-chip-disposing-and-sucking-mechanism horizontal motor 253, so that the analysis-container holding and sucking mechanism 240 is positioned below the discharging mechanism 290.

The dispenser 50 is inserted into the analysis-container main body 720 to discharge the sample (an item (f) of FIG. 5B) while opening the discharging-mechanism discharging valve 294 and the analysis-container-holding-and-sucking-mechanism sucking valve 244 so as to generate the airflow from the discharging mechanism 290 to the analysis-container holding and sucking mechanism 240.

When the discharging of the sample is completed, the dispenser 50 is moved up so that the airflow is once stopped. The sample-container holding and sucking mechanism 230, the analysis-container holding and sucking mechanism 240, and the dispensing-chip disposing and sucking mechanism 250 are moved along the sucking mechanism guide 261 by operating the sample-container-holding-and-sucking-mechanism horizontal motor 233, the analysis-container-holding-and-sucking-mechanism horizontal motor 243, and the dispensing-chip-disposing-and-sucking-mechanism horizontal motor 253, so that the analysis-container holding and sucking mechanism 240 is positioned below the second plug-removing and discharging mechanism 220.

The second plug-removing and discharging mechanism 220 is moved down by operating the second plug-removing-and-discharging-mechanism vertical motor 222 while opening the second plug-removing-and-discharging-mechanism discharging valve 224 and the analysis-container-holding-and-sucking-mechanism sucking valve 244 so as to discharge the air by the second plug-removing and discharging mechanism 220 and so as to suck the air by the analysis-container holding and sucking mechanism 240, so that the analysis container plug 721 is applied to the analysis-container main body 720 (an item (g) of FIG. 5C).

At the same time, the dispenser 50 disposes the dispenser chip 60 to the dispensing-chip disposing container 256 while opening the discharging-mechanism discharging valve 294 and the dispensing-chip-disposing-and-sucking-mechanism sucking valve 254 so as to discharge the air by the discharging mechanism 290 and so as to suck the air by the dispensing-chip disposing and sucking mechanism 250.

Then, the first plug-removing and discharging mechanism 210 and the sample-container holding and sucking mechanism 230 start a plug removing operation for the next sample container, and the second plug-removing and discharging mechanism 220 and the analysis-container holding and sucking mechanism 240 move down and convey the analysis container and returns the dispenser 50 to the initial position.

In the present embodiment, the airflow is controlled upon the plug removal (the item (b) of FIG. 5A) of the first sample-container main body 710 and the plug application (the item (d) of FIG. 5B) of the same, upon the sample sucking from the sample-container main body 710 (the item (c) of FIG. 5A), upon the sample discharging to the analysis-container main body 720 (the item (f) of FIG. 5B), upon the plug application to the analysis-container main body 720, and upon the disposing of the dispensing chip 60 to the dispensing-chip disposing container 256 by the dispenser 50 so that the sample is not peripherally scattered.

The removed sample container plug 711 is held by the first plug-removing and discharging mechanism 210 but is not moved except during the airflow control, and the dispenser 50 is not moved in the sample-holding state except during the airflow control, either. Therefore, there is no concern for the scattering of the sample.

The airflow may be controlled at not only the timing described in the present embodiment but also any timing as similar to the first embodiment. Also, the discharged air volume and the sucked air volume can be also adjusted as similar to the first embodiment, and not the discharging but only the sucking may be performed.

Third Embodiment

In the present embodiment, an example of a device in which a sample is dispensed from a plug-applied sample container to an analysis container without a plug will be explained. Furthermore, a sample processing device in which the sample is dispensed from an analysis container to a series of reaction containers will be also explained.

Figure 6:
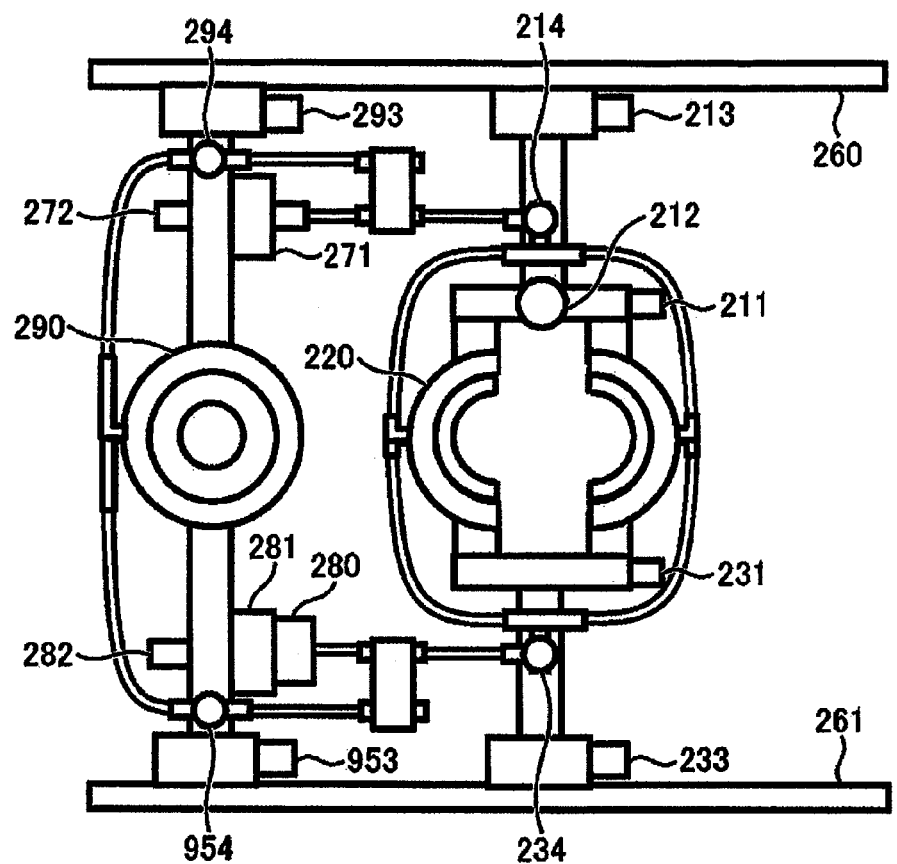
FIG. 6 is detailed diagrams of a sample processing unit according to an embodiment of the present invention, viewed from above and side.
Figure 6:
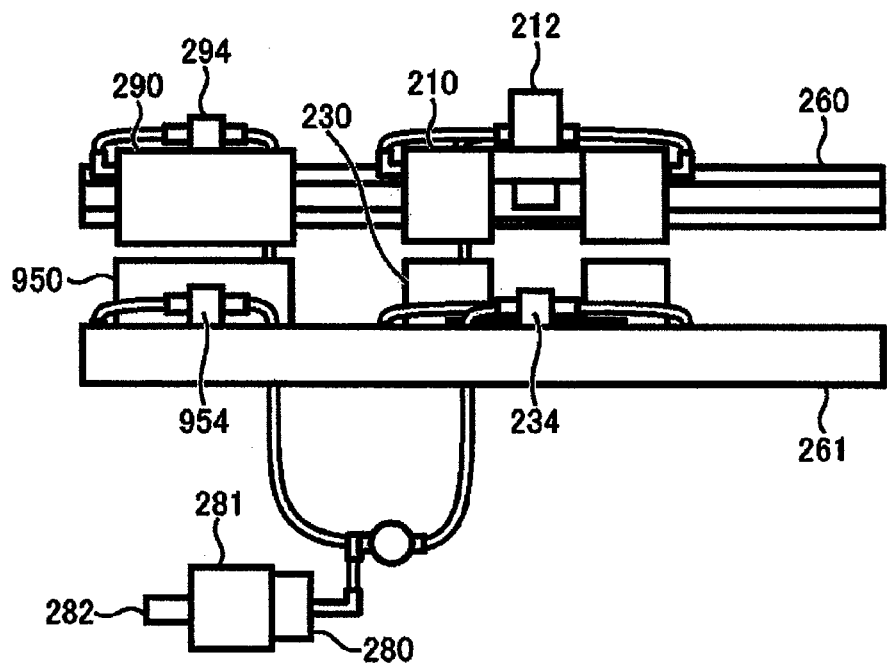

FIG. 6 illustrates details of a sample processing unit according to a third embodiment of the present invention. This embodiment is different from the second embodiment in that there are no second plug-removing and discharging mechanism, no peripheral mechanism of the second plug-removing and discharging mechanism, no analysis-container holding and sucking mechanism, and no peripheral mechanism of the analysis-container holding and sucking mechanism, and in that a sucking mechanism 950, which is obtained by turning the discharging mechanism 290 upside down, is provided instead of the dispensing-chip disposing and sucking mechanism and the dispensing-chip disposing container.

Figure 7A:
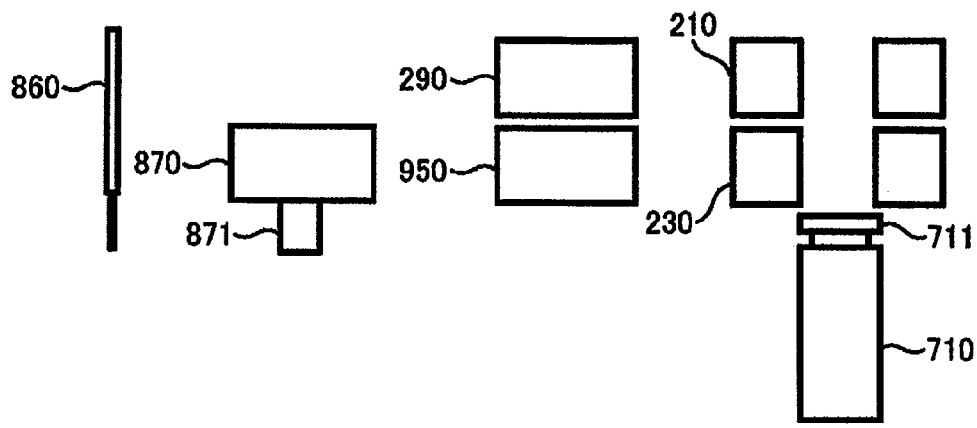
FIG. 7A is operation explanatory diagrams of a sample processing unit according to an embodiment of the present invention.
Figure 7A:
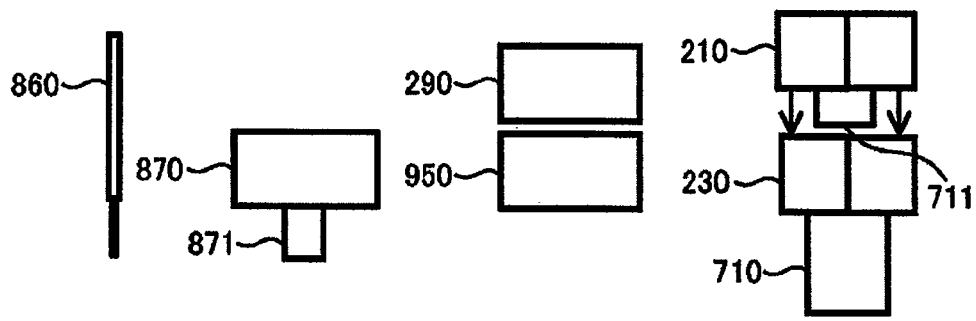
Figure 7A:
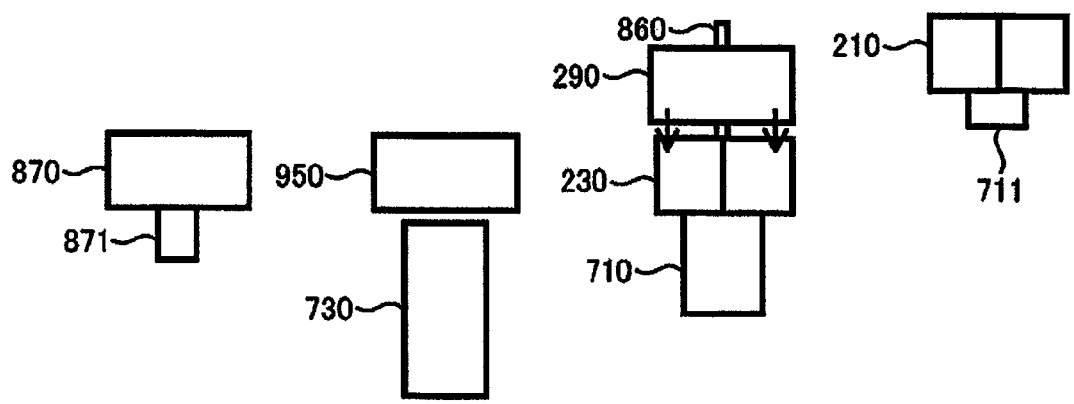

FIGS. 7A and 7B illustrate operations of the sample processing unit according to the third embodiment of the present invention. The drawings illustrate side views of the sample processing unit, and each of the discharging mechanisms, the valves of the sucking mechanisms, the motors, the air pipes, the guides, etc. is omitted.

An item (a) of FIG. 7A illustrates an initial state in which each of the plug-removing and discharging mechanism 210 and the sample-container holding and sucking mechanism 230 is opened, and in which the sample-container main body 710 with being sealed by the sample container plug 711 is set below the plug-removing and discharging mechanism 210 and the sample-container holding and sucking mechanism 230. Cleaning water is supplied to a (nozzle) cleaning tank 870 from a pipe 871, and a tip of the dispenser 860 is cleaned.

The sample-container main body 710 is moved up, and the plug-removing and discharging mechanism 210 and the sample-container holding and sucking mechanism 230 are closed by operating the plug-removing-and-discharging-mechanism opening/closing motor 211 and the sample-container-holding-and-sucking-mechanism opening/closing motor 231, so that the sample container plug 711 and the sample-container main body 710 are held, respectively.

The plug-removing and discharging mechanism 210 is moved up by operating the plug-removing-and-discharging-mechanism vertical motor 212 while opening the plug-removing-and-discharging-mechanism discharging valve 214 and the sample-container-holding-and-sucking-mechanism sucking valve 234 so as to discharge the air by the plug-removing and discharging mechanism 210 and so as to suck the air by the sample-container holding and sucking mechanism 230, so that the sample container plug 711 is removed (an item (b) of FIG. 7A).

Next, the plug-removing-and-discharging-mechanism discharging valve 214 and the sample-container-holdingand-sucking-mechanism sucking valve 234 are once closed, so that the airflow between the plug-removing and discharging mechanism 210 and the sample-container holding and sucking mechanism 230 is stopped. The plug-removing and discharging mechanism 210 and the discharging mechanism 290 are moved along the sucking mechanism guide 260 by operating the plug-removing-and-discharging-mechanism horizontal motor 213 and the discharging-mechanism horizontal motor 293, so that the discharging mechanism 290 is stopped immediately above the sample-container holding and sucking mechanism 230, that is, immediately above the plug-removed sample-container main body 710.

The dispenser 860 is inserted into the sample-container main body 710 to suck the sample (an item (c) of FIG. 7A) while opening the discharging-mechanism discharging valve 294 and the sample-container-holding-and-sucking-mechanism sucking valve 234 so as to generate the airflow from the discharging mechanism 290 to the sample-container holding and sucking mechanism 230. At the same time, the analysis container 730 is set immediately below the sucking mechanism 950.

When the sucking of the sample is completed, the dispenser 860 is moved up so that the airflow is once stopped. The plug-removing and discharging mechanism 210 and the discharging mechanism 290 are moved along the sucking mechanism guide 260 by operating the plug-removing-and-discharging-mechanism horizontal motor 213 and the discharging-mechanism horizontal motor 293, so that the discharging mechanism 290 is moved to a position immediately above the sucking mechanism 950.

The dispenser 860 is moved down into the analysis container 730 to discharge the sample (an item (d) of FIG. 7B) while opening the discharging-mechanism discharging valve 294 and a sucking-mechanism sucking valve 954 so as to discharge the air by the discharging mechanism 290 and so as to suck the air by the sucking mechanism 950.

At the same time, the plug-removing and discharging mechanism 210 is moved down by operating the plug-removing-and-discharging-mechanism vertical motor 212 while opening the plug-removing-and-discharging-mechanism discharging valve 214 and the sample-container-holding-and-sucking-mechanism sucking valve 234 so as to discharge the air by the plug-removing and discharging mechanism 210 and so as to suck the air by the sample-container holding and sucking mechanism 230, so that the sample container plug 711 is applied to the sample-container main body 710.

When the discharging of the sample and plug application are completed, the dispenser 860 is moved to the (nozzle) cleaning tank 870, and the tip thereof is cleaned. The airflow is stopped, and the plug-removing and discharging mechanism 210 and the sample-container holding and sucking mechanism 230 are opened by operating the plug-removing-and-discharging-mechanism opening/closing motor 211 and the sample-container-holding-and-sucking-mechanism opening/closing motor 231, so that the sample-container main body 710 is moved down (an item (e) of FIG. 7B). The analysis container 730 is also moved down.

In the present embodiment, the airflow is controlled so that the sample is not peripherally scattered upon the plug removal (an item (b) of FIG. 7A) of the sample-container main body 710 and the plug application (an item (d) of FIG. 7B) of the same, upon the sample sucking from the sample-container main body 710 (an item (c) of FIG. 7A), and upon the sample discharging to the analysis container 730 (an item (d) of FIG. 7B).

The airflow may be controlled at not only the timing described in the present embodiment but also any timing as similar to the first embodiment. Also, the discharged air volume and the sucked air volume can be also adjusted as similar to the first embodiment, and not the discharging but only the sucking may be performed.

In the embodiment illustrated in FIGS. 7A and 7B, no plug is applied to the analysis container 730. This is because the sample inside the analysis container 730 is used immediately after the sample dispensing by the processing operations of FIGS. 7A and 7B is completed.

Figure 8:
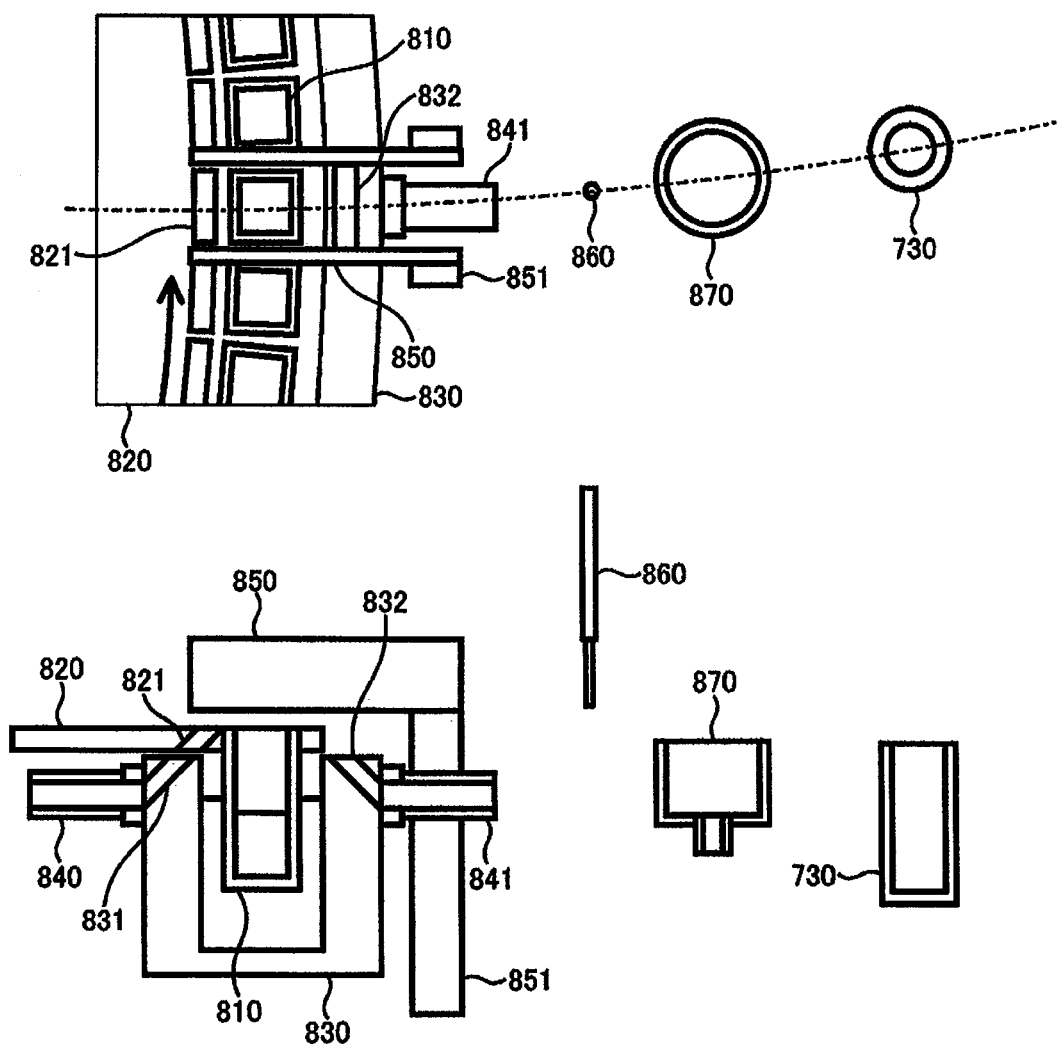
FIG. 8 is configuration diagrams of a dispensing unit of an analysis device according to an embodiment of the present invention, viewed from above and side.

FIG. 8 illustrates an example of an analysis device using the analysis container 730 after the processing operations of FIGS. 7A and 7B. An upper drawing is a top view, and a lower drawing is a side view.

The sample has been dispensed into the analysis container 730 in the processing operations of FIGS. 7A and 7B. The sample inside the analysis container 730 is sucked by the dispenser 860, and is discharged into the reaction container 810. Many reaction containers 810 are circumferentially arranged in the outer peripheral side of a reaction disk 820 which can rotate, and are maintained at a constant temperature by hot water in a constant-temperature bath 830.

The reaction disk 820 is provided with reaction-disk airflow sucking units 821 of the same number as the number of the reaction containers in the inner peripheral side of the reaction containers 810, the reaction-disk airflow sucking units being grooves each having substantially the same width as a width of each of the reaction containers 810, and the reaction-disk airflow sucking units 821 penetrate through the reaction disk 820. On the inner peripheral side of the reaction disk of the constant-temperature bath 830, a constant-temperature bath airflow-sucking-unit inner peripheral side 831, which is a groove having substantially the same width as the width of the reaction container 810, is provided and is connected to an inner-peripheral-side duct 840.

On the reaction-disk outer peripheral side of the constant-temperature bath 830, a constant-temperature bath airflow-sucking-unit outer peripheral side 832, which is a groove having substantially the same width as the width of the reaction container 810, is provided at a position facing the constant-temperature bath airflow-sucking-unit inner peripheral side 831 so as to interpose the reaction container 810 therebetween. The constant-temperature bath airflow-sucking-unit outer peripheral side 832 is connected to an outer-peripheral-side duct 841.

Two facing partitions 850, which are distant from each other by substantially the same width as the width of the reaction container 810, are provided above the constant-temperature bath airflow-sucking-unit outer peripheral side 832, and are supported by supports 851. The partitions are configured to partition the adjacent reaction containers at least from the reaction-disk airflow sucking unit 821 to the constant-temperature bath airflow-sucking-unit outer peripheral side 832.

The dispenser 860 is moved in almost the center between the two partitions 850, is stopped immediately above the reaction container 810, is moved down to the inside thereof, and discharges the sample. At this time, an air-discharge fan (not illustrated) connected to the inner-peripheral-side duct 840 and the outer-peripheral-side duct 841 is operated, so that the air is sucked from the reaction-disk airflow sucking unit 821 and the constant-temperature bath airflow-sucking-unit outer peripheral side 832.

Even if the mist is generated upon the sample discharging by the dispenser 860, the contamination to the adjacent reaction container can be prevented because of the partitions 850, and besides, the mist is not peripherally scattered since the mist is sucked from the reaction-disk airflow sucking unit 821 and the constant-temperature bath airflow-sucking-unit outer peripheral side 832.

The dispenser 860 which has completed the discharge is cleaned by the (nozzle) cleaning tank 870, and, subsequently, the sucking of the sample from the analysis container and the discharging of the sample to the reaction container are repeated. The reaction disk is rotated, and the reaction containers to which the samples are to be dispensed are moved. However, upon the sample discharging, the air is always sucked by the reaction-disk airflow sucking unit 821 corresponding to the reaction container and the constant-temperature bath airflow-sucking-unit outer peripheral side 832 which is fixed to the constant-temperature bath, and therefore, the mist is removed even if the mist of the sample is generated upon the discharging, so that the contamination to the adjacent container does not occur.

Figure 9:
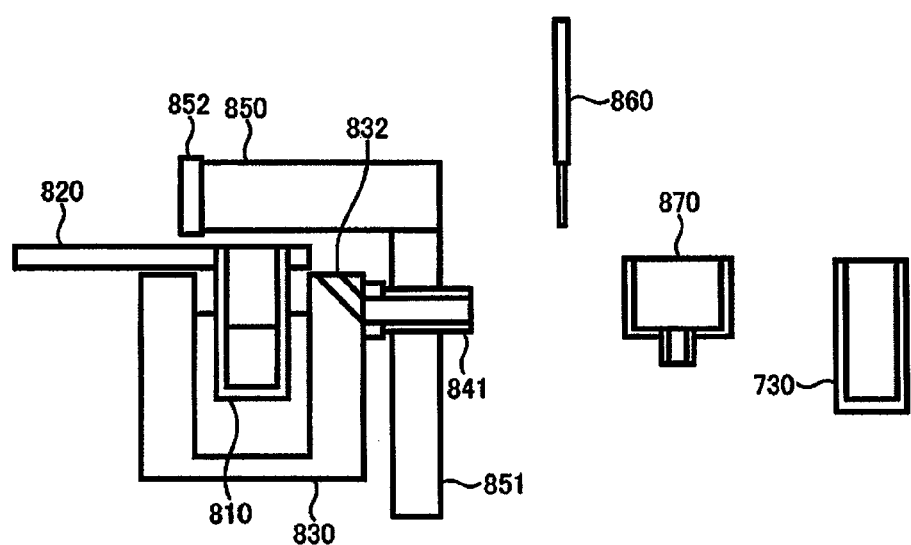
FIG. 9 is configuration diagrams of a dispensing unit of an analysis device according to an embodiment of the present invention, viewed from above and side.
Figure 9:
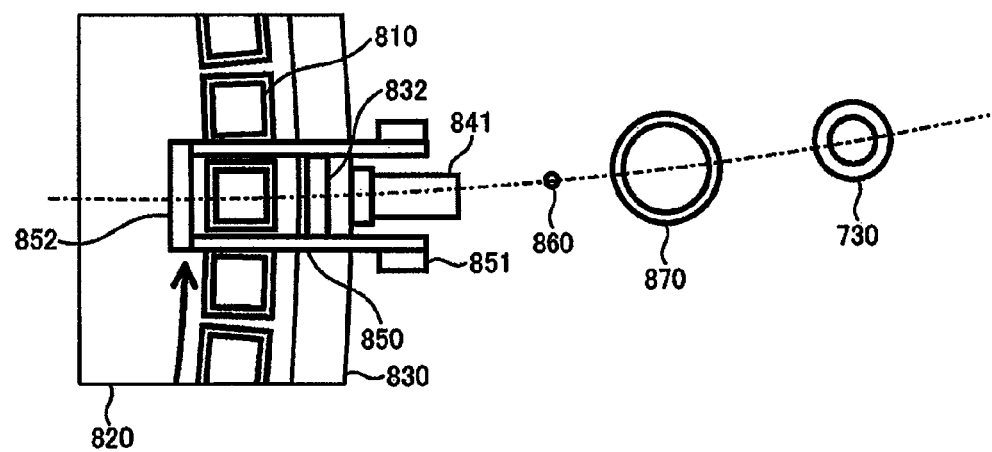

Alternatively, instead of the air sucking by the reaction-disk airflow sucking unit 821, an inner-peripheral partition 852 as illustrated in FIG. 9 may be attached to the partition 850. In this manner, the mist can be removed by the air sucking from the constant-temperature bath airflow-sucking-unit outer peripheral side 832 without providing the penetrating part such as the reaction-disk airflow control unit 821 to the reaction disk 820.

In the present invention, note that the method of removing the mist has been described in the case in which a predetermined amount of the sample is sucked from the container storing the sample and is discharged to another container. However, the present invention is not limited to the contamination of the sample. For example, the methods of the present invention can be also applied to a case in which there is concern for generation of mist of a reagent when the plug of the plug-applied reagent is removed.

SYMBOL EXPLANATION

10 sample processing device
20 sample processing unit
210 first plug-removing and discharging mechanism
220 second plug-removing and discharging mechanism
230 sample-container holding and sucking mechanism
240 analysis-container holding and sucking mechanism
250 dispensing-chip disposing and sucking mechanism
290 discharging mechanism

The invention claimed is:

1. A sample processing device comprising:
   a dispenser sucking liquid from a first container housing the liquid and discharging the liquid to a second container;
   a first holding mechanism that holds the first container;
   a second holding mechanism that holds the second container;
   an air sucking mechanism; and
   a control mechanism which controls the air sucking mechanism,
   wherein the air sucking mechanism includes:
      a first air sucking opening disposed on the first holding mechanism,
      a second air sucking opening disposed on the second holding mechanism,
      an exhaust fan connected by piping to the first and second air sucking openings to suck air from the first and second air sucking openings and discharge the air to outside of the sample processing device,
      a first valve arranged in the piping between the first air sucking opening disposed around the outer wall of the first container and the exhaust fan, and
      a second valve arranged in the piping between the second air sucking opening disposed around the outer wall of the second container and the exhaust fan,
   wherein the control mechanism is configured to control the first holding mechanism to hold the first container so that the first air sucking opening is disposed around an outer wall of the first container and the dispenser to pass through the first holding mechanism and into the first container to suck the liquid from the first container,
   wherein the control mechanism is configured to control the second holding mechanism to hold the second container so that the second air sucking opening is disposed around an outer wall of the second container and the dispenser to pass through the second holding mechanism and into the second container to discharge the liquid into the second container, and
   wherein the control mechanism is configured to control the first valve to open and the exhaust fan to suck the air from the first air sucking opening to generate a downward airflow around a periphery of the dispenser into the first air sucking opening when sucking the liquid with the dispenser from the first container, and to control the second valve to open and the exhaust fan to suck the air from the second air sucking opening to generate a downward airflow around a periphery of the dispenser into the second air sucking opening when discharging the liquid with the dispenser to the second container, thereby sucking the liquid spilled out from the first container by the liquid being sucked by the dispenser from the first container and mist of the liquid being sucked by the dispenser, or sucking the liquid spilled out from the second container by the liquid being discharged by the dispenser into the second container and mist of the liquid being discharged by the dispenser.

2. The sample processing device according to claim 1, further comprising:
   a discharging mechanism positioned above an opening of the first container or the second container that discharges a gas towards the first or second air sucking openings.

3. The sample processing device according to claim 2,
   wherein the control mechanism is further configured to control the discharging mechanism to discharge the gas to generate the downward airflow from a position higher than an opening of the first container or the second container toward the first or second air sucking openings which are respectively located lower than the opening of the first container or the second container.

4. The sample processing device according to claim 3,
   wherein the dispenser has a member positioned above the first container in a state in which the liquid is sucked from the first container,
   wherein one of the member and the first holding mechanism has the air sucking mechanism and/or the discharging mechanism, and
   wherein the control mechanism controls the air sucking mechanism and/or the discharging mechanism to generate the downward airflow that flows from the member toward the first holding mechanism.

5. The sample processing device according to claim 3,
wherein the dispenser has a member positioned above the second container in a state in which the liquid is discharged to the second container,
wherein one of the member and the second holding mechanism has the air sucking mechanism and/or the discharging mechanism, and
wherein the control mechanism controls the air sucking mechanism and/or the discharging mechanism to generate the downward airflow that flows from the member toward the second holding mechanism.

6. The sample processing device according to claim 2,
wherein the second holding mechanism holds a plurality of the second containers, and has a moving mechanism that moves any of the second containers on the second holding mechanism to a position at which the liquid is discharged by the dispenser, and
wherein a partition is provided between a specific one of the second containers stopped at the discharging position and another one of the second containers adjacent to the specific one of the second containers.

7. The sample processing device according to claim 1,
wherein each of the first holding mechanism and the second holding mechanism comprises two semicircular shaped gripping portions that grip the respective first container or second container when engaged, and
wherein the first and second air sucking openings respectively surround a periphery of each of the two semicircular shaped gripping portions of each of the first holding mechanism and the second holding mechanism.

8. The sample processing device according to claim 1,
wherein the first and second air sucking openings face upwards.

9. A sample processing device comprising:
a first holding mechanism that holds a first container which contains a liquid;
a second holding mechanism that holds a second container;
a dispenser that sucks the liquid from the first container and discharges the liquid into the second container;
a plurality of air sucking openings including one or more first air sucking openings that are disposed on the first holding mechanism and one or more second air sucking openings that are disposed on the second holding mechanism;
an exhaust fan connected by piping to suck air into the air sucking openings and discharge the air outside of the sample processing device; and
a plurality of valves disposed in the piping between the air sucking openings and the exhaust fan,
wherein the first holding mechanism holds the first container in a state where the one or more first air sucking openings are disposed around a periphery of an outer wall of the first container and the dispenser passes through the first holding mechanism and into the first container to suck the liquid from the first container,
wherein the second holding mechanism holds the second container in a state where the one or more second air sucking openings are disposed around a periphery of an outer wall of the second container and the dispenser passes through the second holding mechanism and into the second container to discharge the liquid into the second container,
wherein a first one of the valves opens and the exhaust fan sucks the air from the first air sucking openings to generate a downward airflow around the dispenser into the first air sucking openings when sucking the liquid from the first container, and a second one of the valves opens and the exhaust fan sucks the air from the second air sucking openings to generate a downward airflow around the dispenser into the second air sucking openings when discharging the liquid into the second container with the dispenser, thereby sucking the liquid spilled out from the first container by the liquid being sucked by the dispenser from the first container and mist of the liquid being sucked by the dispenser, or sucking the liquid spilled out from the second container by the liquid being discharged by the dispenser into the second container and mist of the liquid being discharged by the dispenser.

10. The sample processing device according to claim 9, further comprising:
a discharging mechanism positioned above an opening of the first container or the second container that discharges air into the downward airflow towards at least one of the first or second air sucking openings,
wherein the at least one of the first or second air sucking openings faces upwards towards the discharging mechanism.

11. The sample processing device according to claim 1,
wherein the first holding mechanism holds a top of the first container and the dispenser passes through the first holding mechanism and into the top of the first container to suck the liquid from the first container, and
wherein the second holding mechanism holds a top of the second container and the dispenser passes through the second holding mechanism and into the top of the second container to discharge the liquid into the second container.

12. The sample processing device according to claim 9,
wherein the first holding mechanism holds a top of the first container and the dispenser passes through the first holding mechanism and into the top of the first container to suck the liquid from the first container, and
wherein the second holding mechanism holds a top of the second container and the dispenser passes through the second holding mechanism and into the top of the second container to discharge the liquid into the second container.

* * * * *